US00PP31085P2

(12) United States Plant Patent
Olesen et al.

(10) Patent No.: US PP31,085 P2
(45) Date of Patent: Nov. 19, 2019

(54) ***CLEMATIS* PLANT NAMED 'EVIPO096'**

(50) Latin Name: *Clematis integrifolia*
Varietal Denomination: Evipo096

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,902

(22) Filed: Sep. 10, 2018

(51) Int. Cl.
*A01H 5/00* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 5/02; A01H 5/00
See application file for complete search history.

(56) References Cited

PUBLICATIONS https://www.rhs.org.uk/plants/pdfs/plant-register-supplements/Clematis/6th-Clematis-Supplement.pdf; 2018; 1 page.*

* cited by examiner

*Primary Examiner* — Kent L Bell

(57) ABSTRACT

A new *Clematis* plant with a compact growth habit, profuse, Violet Blue flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

1 Drawing Sheet

Botanical classification:
Genus: *Clematis.*
Species: *integrifolia.*
Variety denomination: 'Evipo096'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 1995 and the resulting seeds were planted the following winter in a controlled environment in Guernsey, Channel Islands, United Kingdom. The new variety named 'Evipo096' originated as a single seedling from the stated cross.

The new *clematis* plant may be distinguished from its female seed parent and male pollen parent by the following characteristics. The female seed parent has flower pedicels over 120 mm in length while the new variety has pedicels which are 100 to 115 mm in length. The male seed parent has Red-Purple flowers while the new variety has Violet Blue tepals.

The objective of the hybridization of this *clematis* plant was to create a new and distinct variety for nursery culture with unique qualities such as:

1. Uniform and abundant Violet Blue flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo096' was selected by Mogens N. Olesen and Raymond J. Evison in their *clematis* development program in the Channel Islands, United Kingdom in 1996. Asexual reproduction of 'Evipo096' by means of vegetative cuttings and traditional layering was first performed by Mogens N. Olesen and Raymond J. Evison in the nursery during the summer of 1996. This initial and subsequent asexual propagations have demonstrated that the characteristics of 'Evipo096' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo096'. Specifically illustrated in the drawing are open flowers, petals detached, reproductive flower parts, leaves, and stems. Illustrated plants are 2 years of age.

DETAILED DESCRIPTION OF THE VARIETY

The following is a detailed description of 'Evipo096', as observed in its growth throughout the flowering period in Marion County Oreg. Observed plants were cultivated for a period of 24 months in an open field. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of an unnamed plant of *Clematis integrifolia* are compared to 'Evipo096' in Chart 1.

CHART 1

| | 'Evipo096' | an unnamed plant of *Clematis integrifolia* |
|---|---|---|
| Flower diameter | 70 mm | 80 mm |
| Tepal upper surface | Violet-Blue 93C | Violet 91A |
| Tepal count | 4 | 4 |

FLOWER AND FLOWER BUD

Blooming habit: Recurrent. The natural flowering period is generally from May to September.

Flower bud:
- *Size*.—Normally 30 mm in length. Bud diameter is 13 mm.
- *Bud form*.—Campanulate, broad based.
- *Bud color*.—Greyed-Purple Group N186B.
- *Texture*.—Pubescent.

Pedicel:
- *Surface texture*.—Ribbed.
- *Length*.—On average 100 to 115 mm in length with 3 mm diameter.
- *Color*.—Yellow-Green Group 144B with intonations of Greyed-Purple Group N186B.
- *Strength*.—Strong.

Receptacle:
- *Surface texture*.—Lightly pubescent.
- *Shape*.—Broad funnel.
- *Size*.—2 mm (h)×2 mm (w).
- *Color*.—Yellow-Green Group 144B with intonations of Greyed-Purple Group N186B.

Flower arrangement:
- *Location on plant*.—New growth only, dichasial cyme.
- *Borne*.—Singly.

Flower bloom:
- *Size*.—On average, flowers are 70 mm in diameter and 45 mm in depth.
- *Profile*.—Open flowers are nodding, urceolate.
- *Fragrance*.—None.
- *Lasting quality*.—Flowers normally remain up to 10 days on the plant.

Tepals:
- *Tepal color*.—The upper surface is Violet-Blue 93C with a basal tepal spot of White Group N155A. The lower surface is Violet-Blue 93D at margins, with a central bar of Violet Group N88A.
- *Quantity*.—Normally 4 tepals.
- *Size*.—56 mm in length by 22 mm wide.
- *Shape*.—Individual tepal shape is oblanceolate. The tepal apex is acute. The tepal base is flat.
- *Apex recurvature*.—Recurved strongly.
- *Tepal cross section*.—Slightly reflexed, somewhat twisted.
- *Margins*.—Entire, with strong undulations.
- *Texture*.—Rugose
- *Persistence*.—Tepals are self cleaning. .

Reproductive organs:
- *Pollen*.—None observed.
- *Anthers*.—Size: 6 mm in length. Color: Yellow Group 4C. Quantity: On average, 30.
- *Filaments*.—Color: Yellow Group 4D. Length: 8 mm.
- *Pistils*.—Quantity: On average, 12.
- *Stigmas*.—Inferior in location relative to the length of the filaments and the height of the anthers.
- *Styles*.—Color: Green-White Group 157A. Length: About 14 mm.

Seed head characteristics: Seed not observed to date.

PLANT

Plant form: Upright.

Plant growth: Moderately vigorous.

Size: Seasons growth attains 55 cm in height. Average spread is 45 cm.

Stems:
- *Color*.—Juvenile stems are Yellow-Green Group 144C. Mature stems are Yellow-Green Group 144C with intonations of Greyed-Purple Group N186A.
- *Internodes*.—On average, 7 cm between nodes.
- *Length*.—Normally 30 cm from the base of the plant to the flowering portion of the stem.
- *Diameter*.—About 5 mm.
- *Texture*.—Mature stems are ribbed.

Plant foliage:
- *Leaf characteristics*.—Deciduous.
- *Arrangement*.—Opposite, simple, sessile.
- *Leaf size*.—Leaves are about 95 to 100 mm (l)×55 mm (w).
- *Abundance*.—On average 2 leaves per 10 cm of stem.
- *Leaf color*.—Juvenile upper Yellow-Green Group 144B. Juvenile lower Yellow-Green Group 144B. Mature upper Yellow-Green Group 146A. Mature lower Yellow-Green Group 147C.
- *Stipules*.—Absent.
- *Petioles*.—None.
- *Leaflet shape*.—Deltoid and elliptic. The base is rounded, apex acute.
- *Margin*.—Entire, lightly pubescent.
- *Surface*.—Rugose.
- *Thickness*.—Moderate.
- *Glossiness*.—Moderately glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo096', substantially as described and illustrated, due to its abundant Violet Blue flowers with good keepability, attractive long lasting foliage and compact growth, year round flowering under glasshouse conditions, suitability for production from softwood cuttings in pots, durable flowers and foliage which make the variety suitable for distribution in the floral industry.

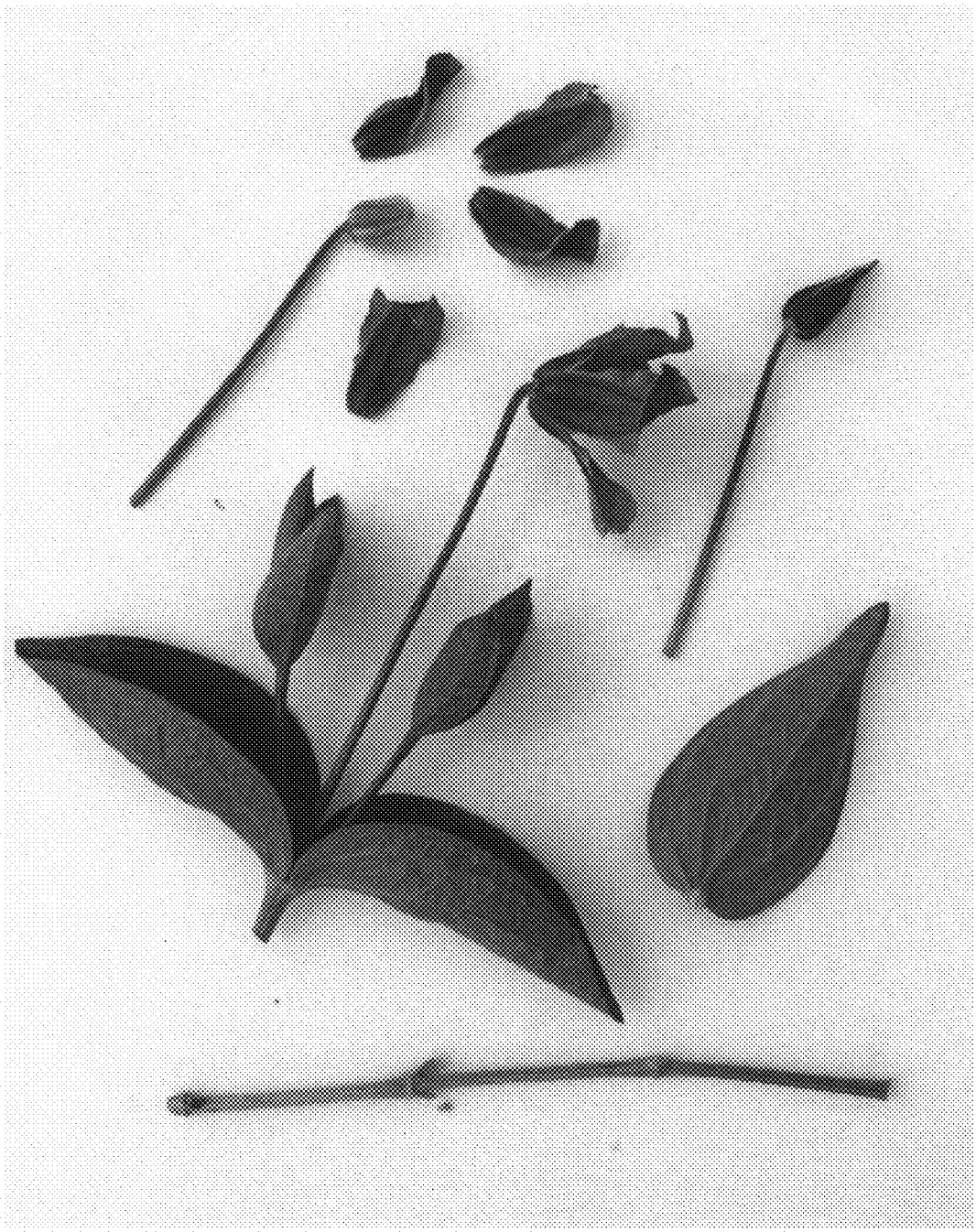

* * * * *